United States Patent [19]
Delprato et al.

[11] Patent Number: 5,693,846
[45] Date of Patent: Dec. 2, 1997

[54] PROCESS FOR PREPARATION OF 4-MERCAPTO-1-NAPHTHOL COMPOUNDS

[75] Inventors: Ivano Delprato, Rocchetta Di Cairo Montenotte(Savona); Massimo Bertoldi, Fossano (Cueno), both of Italy

[73] Assignee: Imation Corp., Oakdale, Minn.

[21] Appl. No.: 693,838

[22] Filed: Aug. 1, 1996

[30] Foreign Application Priority Data

Sep. 18, 1995 [EP] European Pat. Off. .............. 95114619

[51] Int. Cl.⁶ .................................................. C07C 331/00
[52] U.S. Cl. ........................... 560/10; 564/162; 564/182; 564/184; 564/99
[58] Field of Search ............................... 564/162, 184, 564/182, 99; 560/18, 910

[56] References Cited

U.S. PATENT DOCUMENTS

| | | |
|---|---|---|
| 3,227,554 | 1/1966 | Barr et al. . |
| 3,701,783 | 10/1972 | Barr et al. . |
| 4,248,962 | 2/1981 | Lau . |
| 4,293,691 | 10/1981 | Furutachi et al. . |
| 4,409,323 | 10/1983 | Sato et al. . |
| 4,865,959 | 9/1989 | Sakanoue et al. . |

FOREIGN PATENT DOCUMENTS

| | | |
|---|---|---|
| 0 193 389 A2 | 2/1986 | European Pat. Off. . |
| 9972/89 | 1/1989 | Japan . |

*Primary Examiner*—Samuel Barts
*Attorney, Agent, or Firm*—Gregory A. Evearitt; Arlene K. Musser

[57] ABSTRACT

A process for preparation of 4-mercapto-1-naphthol compounds which comprises the steps of:

(i) obtaining a 4-heterocyclylthio-1-naphthol compound by reacting a 1-naphthol compound with a heterocyclylsulfur chloride or by reacting a 4-iodo-1-naphthol compound with an alkali metal or ammonium salt of a mercaptoheterocyclic compound, (ii) hydrolyzing the resulting 4-heterocyclylthio-1-naphthol compound in the presence of a base to form a reaction product, and (iii) acidifying said reaction product.

The resulting compounds are useful as intermediates in the synthesis of bleach accelerator releasing couplers for use in silver halide color photographic materials.

11 Claims, No Drawings

PROCESS FOR PREPARATION OF 4-MERCAPTO-1-NAPHTHOL COMPOUNDS

FIELD OF THE INVENTION

This invention relates to a process for the preparation of 4-mercapto-1-naphthol compounds. Such compounds are useful as intermediates for formation of photographic couplers, in particular bleach accelerator releasing couplers.

BACKGROUND OF THE INVENTION

Silver halide color photographic materials useful for forming dye images are fundamentally processed by a color developing step and a desilvering step after imagewise exposure. In the color development step, exposed silver halides in the photographic material are reduced by color developing agents to form silver and at the same time the oxidized color developing agents react with dye-forming couplers in the photographic material to form dye images. In the subsequent desilvering step, silver is oxidized by a bleaching agent and further converted into a water soluble silver complex by a fixing agent and dissolved off. Such materials and processes are described in, for example, The Theory of the Photographic Processes, 4th ed., T. H. James, 1977, pages 462–463 and pages 335–361.

Bleach accelerator releasing couplers, also known as BARC, are known to improve the desilvering property of photographic materials. These bleach accelerator releasing couplers contain a bleach accelerator moiety which is released upon reaction with the oxidized color developing agent. Examples of such couplers are described in, for example, Research Disclosure 11449, EP 193,389 and U.S. Pat. No. 4,865,959. An example of one such coupler, described in EP 193,389, is herein designated as BARC A and is represented by the formula

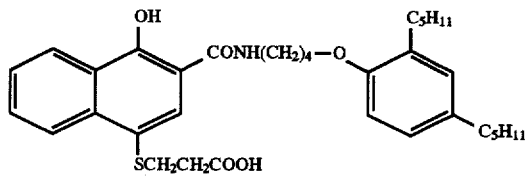

which is prepared by using as an intermediate a 4-mercapto-1-naphthol compound of formula

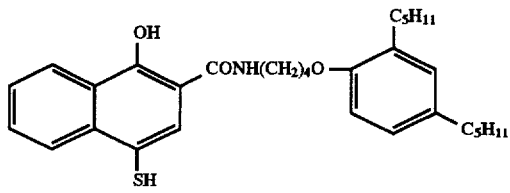

whose preparation or synthesis reference are not, however, reported.

There exists the need for a convenient, efficient and expeditious synthesis of 4-mercapto-1-naphthol compounds as intermediates for such bleach accelerator releasing couplers.

JP 9,972/89 describes a process for preparation of 4-mercapto-1-naphthol compounds in which 1-naphthol compounds are reacted with $S_2Cl_2$ to form polysulfides, followed by reduction with Zn and AcOH to form the 4-mercapto-1-naphthol compound. JP 9,972/89 also reports other literature references to the synthesis of 4-mercapto-1-naphthol compounds which require a reduction step (for example, reduction with $Zn/H_2SO_4$ or $LiAlH_4$).

The present invention provides an improved process for preparation of 4-mercapto-1-naphthol compounds which overcome drawbacks of prior art processes, provides a relatively simple reaction mechanism without a reduction step, avoids the use of non toxic materials, and produces less pollutant waste.

SUMMARY OF THE INVENTION

A process for preparation of 4-mercapto-1-naphthol compounds comprises the steps of:

(i) obtaining a 4-heterocyclylthio-1-naphthol compound by reacting a 1-naphthol compound with a heterocyclylsulfur chloride or by reacting a 4-iodo-1-naphthol compound with an alkali metal or ammonium salt of a mercaptoheterocyclic compound, (ii) hydrolyzing the resulting 4-heterocyclylthio-1-naphthol compound in the presence of a base to form a reaction product, and (iii) acidifying said reaction product.

DETAILED DESCRIPTION OF THE INVENTION

4-Mercapto-1-naphthol compounds, prepared according to the process of the present invention can be represented by the formula (I)

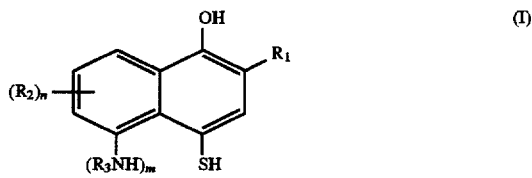

wherein $R_1$ represents —$CONR_4R_5$, —$NHCOR_4$, —$NHCOOR_6$, —$NHSO_2R_6$, —$NHCONR_4R_5$, or —$NHSO_2R_4R_5$, wherein $R_4$ and $R_5$ (which may be the same or different) each represents a hydrogen atom or an aliphatic, aromatic or heterocyclic group, or together $R_4$ and $R_5$ form a ring, and $R_6$ represents an aliphatic, aromatic or heterocyclic group, $R_2$ represents a group capable of substituting for a hydrogen atom of the naphthol ring, n represents 0 or an integer of from 1 to 3 and, when n is 2 or 3, $R_2$'s can be the same or different, or together form a ring, $R_3$ represents a hydrogen atom or a monovalent organic group, and m represents 0 or 1.

In the above-described formula (I), the aliphatic group represented by $R_4$, $R_5$ and $R_6$ is preferably a straight chain, branched chain or cyclic, saturated or unsaturated, and substituted or unsubstituted alkyl, alkenyl or alkynyl group having 1 to 30 carbon atoms. Typical examples thereof include a methyl, ethyl, butyl, cyclohexyl, allyl, propargyl, methoxyethyl, n-decyl, n-dodecyl, n-hexadecyl, trifluoromethyl, heptafluoropropyl, dodecyloxypropyl, 2,4-di-t-amylphenoxypropyl and 2,4-di-t-amylphenoxybutyl group.

The aromatic group represented by $R_4$, $R_5$ and $R_6$ each preferably represents a substituted or unsubstituted aryl group (including a condensed ring) having 6 to 30 carbon atoms. Typical examples thereof include a phenyl, tolyl, 2-tetradecyloxyphenyl, pentafluorophenyl, 2-chloro-5- dodecyloxycarbonylphenyl, 4-chlorophenyl, 4-cyanophenyl and 4-hydroxyphenyl group.

The heterocyclic group represented by $R_4$, $R_5$ and $R_6$ each preferably represents a substituted or unsubstituted monocyclic or condensed heterocyclic ring having 2 to 30 carbon atoms. Typical examples thereof are a 2-pyridyl, 4-pyridyl, 2-furyl, 4-thienyl and quinolinyl group.

$R_4$ and $R_5$ in —$NR_4R_5$ for $R_1$ can together form a nitrogen-containing heterocyclic ring (e.g., a morpholino, piperidino and pyrrolidino ring).

$R_2$ represents a group or atom capable of substituting for a hydrogen atom on the naphthol ring and typically includes a halogen atom, a hydroxyl, amino, carboxyl, sulfo, cyano, aromatic, aliphatic, heterocyclic, carbonamido, sulfonamido, carbamyl, sulfamoyl, ureido, acyloxy, acyl, aliphatic oxy, aromatic oxy, aliphatic thio, aromatic thio, aliphatic sulfonyl, aromatic sulfonyl, sulfamoylamino, nitro and imido group. Preferably, the total number of carbon atoms contained in $R_2$ is from 0 to 30.

The monovalent organic group represented by $R_3$ preferably includes —$COR_7$, —$COOR_4$, —$SO_2R_7$, —$CONR_4R_5$ or —$SO_2R_4R_5$, and $R_7$ represents a hydrogen atom, an aliphatic, aromatic or heterocyclic group as defined above for $R_4$, —$OR_4$, —$COR_4$, —$SO_2R_4$ or —$NR_4R_5$, wherein $R_4$ and $R_5$ areas defined above.

When the term "group" is used in this invention to describe a chemical compound or substituent, the described chemical material includes the basic group and that group with conventional Substitution. When the term "moiety" is used to describe a chemical compound or substituent, only the unsubstituted chemical material is intended to be included. For example, "alkyl group" includes not only such alkyl moiety as methyl, ethyl, octyl, stearyl, etc., but also said moieties bearing substituent groups such as halogen, cyano, hydroxy, nitro, amino, carboxylate, etc. On the other hand, "alkyl moiety" includes only methyl, ethyl, stearyl, cyclohexyl, etc.

Illustrative examples of 4-mercapto-1-naphthol compounds which can be produced according to the present invention are as follows. Each of the following compounds are useful as intermediates in the synthesis of bleach accelerator releasing couplers, as described in EP 193,389.

I-1:

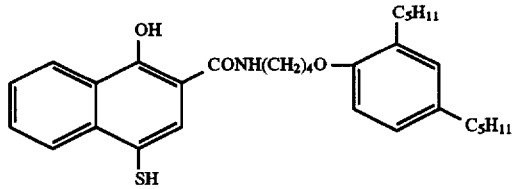

I-2:

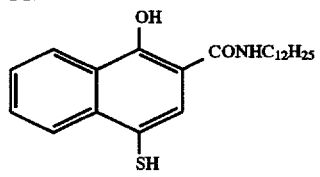

I-3:

-continued

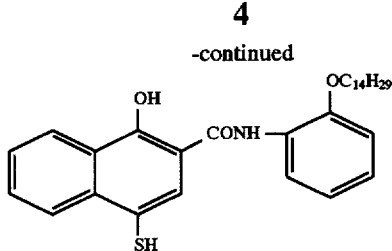

I-4:

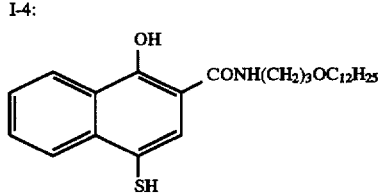

I-5:

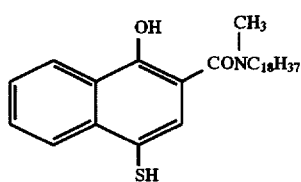

I-6:

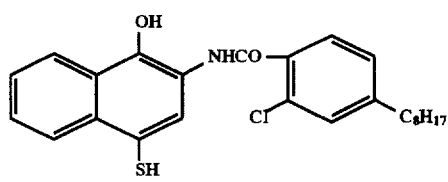

I-7:

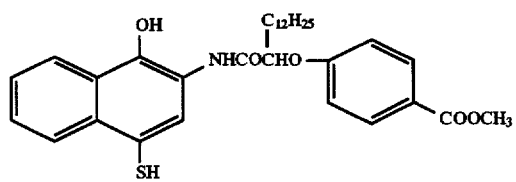

I-8:

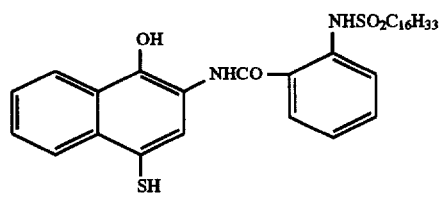

I-9:

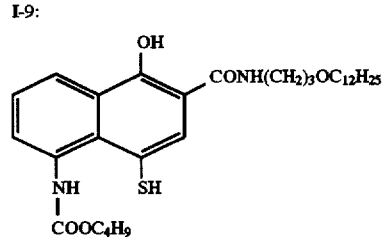

I-10:

-continued

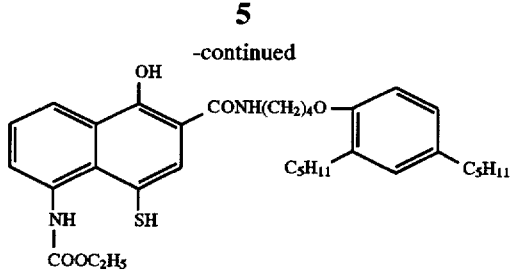

According to the step (i) of the process of the present invention, a 1-naphthol compound of formula (A)

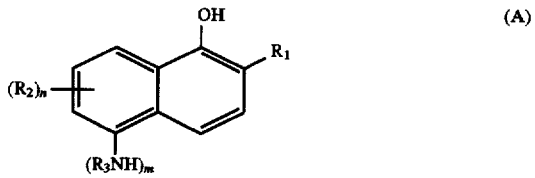 (A)

wherein $R_1$, $R_2$, $R_3$, n and m are as defined above, is reacted with a heterocyclylsulfur chloride of formula (B)

HET—SCl  (B)

wherein HET represents a heterocyclic group, to produce a 4-heterocyclylthio-1-naphthol compound of formula (C)

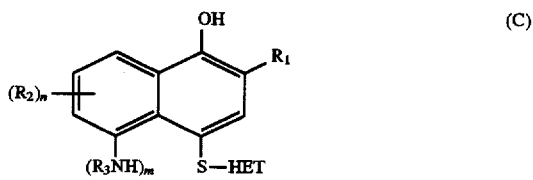 (C)

wherein $R_1$, $R_2$, $R_3$, n, m and HET are as defined above.

Alternatively, according to the step (i) a 4-iodo-1-naphthol compound of formula (D)

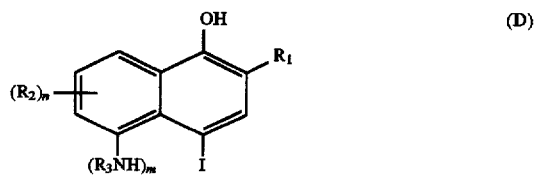 (D)

wherein $R_1$, $R_2$, $R_3$, n and m are as defined above, is reacted with an alkali metal or ammonium salt of a mercaptoheterocyclic compound of formula (E)

HET—S⁻M⁺  (E)

wherein HET represents a heterocyclic group and M represents an alkali metal (such as sodium, potassium, lithium) or ammonium group (such as ammonium, triethylammonium, triethanolammonium), to produce a 4-heterocyclylthio-1-naphthol compound of formula (C) as defined above.

Suitable heterocyclic groups for HET include, for example, a tetrazolyl, triazinyl, triazolyl, oxazolyl, oxadiazolyl, diazolyl, thiazyl, thiadiazolyl, benzoxazolyl, benzotriazolyl, benzothiazolyl, pyrimidyl, pyrimidinyl and quinolyl group. The reaction of step (i) is preferably conducted in an aprotic solvent such as acetonitrile, toluene, dimethylformamide, dimethylacetamide, cyclohexane, diethylether, tetrahydrofuran, chloroform, dioxane and carbontetrachloride. While these solvents are preferred, other solvents which are inert with respect to the reactants and products and satisfactorily dissolve the subjects materials can be employed. The reaction is typically carried out at atmospheric pressure (±700 mmHg) at a temperature within the range from 20° C. to 100° C. and a reaction time of 0.5 to 8 hours.

Compounds of formula (C) which have an heterocyclylthio group attached to the coupling position of the cyan dye-forming 1-naphthol couplers have been known in the photographic art. Examples of such couplers are described in, for example. U.S. Pat. Nos. 3,227,554, 3,701,783 and 4,293,691. These compounds are widely used in the silver halide color photographic materials as development inhibitor releasing (DIR) couplers.

In the subsequent hydrolysis step (ii), compound (C) is hydrolyzed to yield the desired 4-mercapto-1-naphthol compound (I). The reaction is conducted in a suitable solvent such as a protic (e.g., methanol, ethanol, propanol) or aprotic (e.g., acetonitrile, dioxane) solvent which satisfactorily dissolves compounds (C). The reaction is conducted in the presence of about one mole equivalent of an inorganic or organic base, such as alkali metal hydroxides or salts (e.g., sodium hydroxide, potassium carbonate, sodium carbonate) or alkali metal salts of lower alcohols (e.g., sodium methoxide, potassium methoxide, sodium ethoxide). Mild reaction temperatures, such as temperatures within the range from 20° C. to 70° C., are employed at ambient pressure and a reaction time of 0.5 to 4 hours. Next, after the reaction comes to completion, an acid is added to the reaction mass (step iii) to IO achieve a pH below 6 and the 4-mercapto-1-naphthol compound (I) is isolated from the reaction mass either by filtration (if the organic solvent employed is not a solvent for compound (I)) or by removal of the solvent by evaporation (if the organic solvent employed is a solvent for the compound (I) too).

Compounds of formula (I) are useful as intermediates in the synthesis of bleach accelerator releasing couplers (BARC) of the 1-naphthol type having in the coupling position (i.e., the 4-position of the 1-naphthol ring) a releasable bleach accelerator group represented by the formula:

$$-(\text{TIME})_p-S-R_8-R_9$$

wherein

TIME is a timing group, p is 0 or 1, $R_8$ is an alkylene group comprising 1 to 8 carbon atoms, and $R_9$ is a water solubilizing group, preferably a carboxy group.

Preferred releasable bleach accelerator group is represented by the formula:

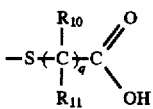

q is 1 to 8, $R_{10}$ and $R_{11}$ are individually hydrogen or alkyl group containing 1 to 4 carbon atoms, and wherein the total number of carbon atoms in $R_{10}-(C)_q-R_{11}$ is 1 to 8.

Alkyl group includes straight or branched chain alkyl groups, such as methyl, ethyl, n-propyl, n-butyl, and t-butyl.

Bleach accelerator releasing couplers can be synthetized from compounds of formula (I) by defined synthetic procedures as exemplified in Example 2 by selection of appropriate reagents.

The bleach accelerator group is attached at the coupling position of the coupler of the coupler which enables the bleach accelerator group to be displayed upon reaction of the coupler with oxidized color developing agent.

In the bleach accelerator releasing coupler, the bleach accelerator can be bonded to the coupler through a timing group (TIME). TIME is a group which enables the timed release of the —S—$R_8$—$R_9$ group from the coupler. The timing mechanism can be any timing mechanism which is useful for releasing photographically useful groups from couplers. For example, the timing mechanism can be as described in, for example, U.S. Pat. Nos. 4,248,962 and 4,409,323.

In the formula of the bleach accelerator group, $R_9$ can optionally be a precursor to a water solubilizing group. For example, $R_9$ can be an ester group which upon hydrolysis forms a water solubilizing carboxylic acid group.

The following $R_9$ groups are examples of useful water solubilizing groups and their precursors:

—COOH
—COOCH$_3$
—COOC$_2$H$_5$
—NHSO$_2$CH$_3$
—SO$_3$H
—OH

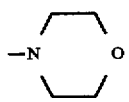

—COO—C$_6$H$_5$
—SO$_2$NH$_2$
—NR$_{12}$R$_{13}$ wherein R$_{12}$ is H or alky of 1 to 4 carbon atoms, R$_{13}$ is alkyl of 1 to 4 carbon atoms and wherein at least one of R$_{12}$ and R$_{13}$ is alkyl, and the total number of carbon atoms in R$_{12}$ and R$_{13}$ is no more than 8.

The following are examples of useful R$_8$ groups:
—CH$_2$—, —CH$_2$CH$_2$—, —CH$_2$CH$_2$CH$_2$—, —CH$_2$CH$_2$CH$_2$CH$_2$—, —CH$_2$CH$_2$OCH$_2$CH$_2$, —CH$_2$CH(CH)$_3$CH$_2$—, —CH$_2$CH(C$_2$H$_5$)CH$_2$CH$_2$—, —CH(CH$_3$)CH$_2$—, —CH$_2$CH$_2$CH(CH$_3$)CH$_2$—.

The invention is further illustrated by the following examples, without being limited thereby.

EXAMPLE 1

Synthesis of 1-hydroxy-4-mercapto-N-[4-(2,4-di-t-amylphenoxy)-butyl]-2-naphthamide (Compound I-1)

Step (i). To a solution of 47.6 g of 1-hydroxy-N-[4-(2,4-di-t-amylphenoxy)-butyl]-2-naphthamide in 500 ml of carbon tetrachloride, was added a solution of 21 g of 1-phenyl-5-tetrazolylsulfur chloride (prepared according to *Org. Synth. Coll.*, vol. II, page 445) in 200 ml of carbon tetrachloride. The mixture was refluxed overnight and concentrated in vacuo. The solid was recrystallized from 500 ml of acetonitrile, yielding 50 g of 1-hydroxy-4-(1-phenyl-5-tetrazolylthio)-N-[4-(2,4-di-t-amylphenoxy)-butyl]-2-naphthamide of formula

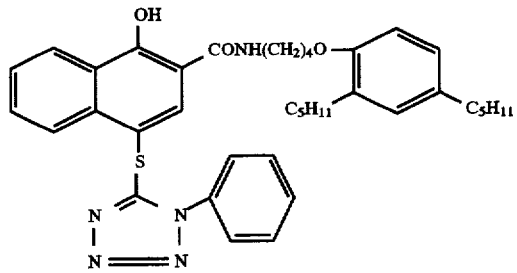

which melted at 147°–148° C. (Synthesis as described in U.S. Pat. No. 3,701,783).

Steps (ii and iii). To a solution of 50 g of 1-hydroxy-4-(1-phenyl-5-tetrazolylthio)-N-[4-(2,4-di-t-amylphenoxy)-butyl]-2-naphthamide in 700 ml ethanol, 300 ml of aqueous 30% by weight NaOH were added under a stream of nitrogen. The mixture was stirred at 60° C. for 90 minutes, then cooled at room temperature and aqueous 37% by weight HCl, was added dropwise and under stirring, until pH 3 was reached. The separated solid was filtered, washed with water, then dissolved in 100 ml methylene chloride. The mixture was filtered and the methylene chloride solution was dried over sodium sulfate and evaporated to dryness. The residue was crystallized from cyclohexane. The yield of compound I-1 was 27.9 g, as white prisms. Proton NMR was consistent with the structure. The compound was also identified by elemental analysis:

$C_{31}H_{41}NO_3S$: Found %C=73.26, %N=2.93, %H=8.31, %S=6.35

Expected %C=73.33, %N=2.76, %H=8.14, %S=6.32

EXAMPLE 2

Synthesis of 1-hydroxy-4-carboxyethylthio-N-[4-(2,4-di-t-amylphenoxy)-butyl]-2-naphthamide (BARC A)

Ethylacrylate (5.065 g, 0.0506 mol) was added at room temperature under stirring to tetramethylguanidine (7 g, 0.0608 mol) and compound I-1, prepared according to example 1, in tetrahydrofurane (375 ml) under nitrogen stream. After 30 minutes, 50% aqueous sodium hydroxide (10 ml) in methanol (50 ml) was added, and the resulting solution after 15 minutes was poured into 5% aqueous hydrochloric acid. The mixture was extracted with ethylacetate and the organic solution was taken to dryness under vacuum. The residue was crystallized from acetonitrile (150 ml) and then toluene (30 ml) to give 11 g of BARC A, as a white solid. Proton NMR was consistent with the structure. The compound was also identified by elemental analysis:

$C_{34}H_{45}NO_5S$: Found %C=70.55 %H=7.95 %N=2.33 %S=5.68

Required %C=70.43 %H=7.82 %N=2.42 %S=5.53

EXAMPLE 3

Synthesis of 1-hydroxy-4-mercapto-2'-tetradecyloxy-2-naphthanilide (Comp. I-3)

Step (i). 1-hydroxy-4-iodo-2'-tetradecyloxy-2-naphthanilide (9 g) and 1-phenyl-5-mercapto-tetrazole potassium salt (3 g) were solubilized im dimethylformamide (25 ml). The solution was heated at 90° C. for 1 hour under stirring. After adding ethanol (25 ml), a white solid precipitated. The solid collected by filtration was crystallized from ethanol. The yield was 90% of 1-hydroxy-4-(1-phenyl-5-tetrazolylthio)-2'-tetradecyloxy-2-naphthanilide of formula

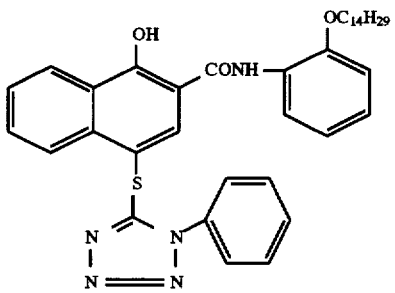

The compound was identified by elemental analysis:

Found: %C=70.29 %H=6.91 %N=10.49

Required: %C=70.02 %H=6.96 %N=10.74

(Synthesis as described in BE 789,595)

Steps (ii and iii). The procedure of Example 1 was repeated to obtain in high yield Compound I-3.

We claim:

1. A process for preparation of 4-mercapto-1-naphthol compounds which comprises the steps of:

(i) obtaining a 4-heterocyclylthio-1-naphthol compound by reacting a 1-naphthol compound with a heterocyclylsulfur chloride or by reacting a 4-iodo-1-naphthol compound with an alkali metal or ammonium salt of a mercaptoheterocyclic compound, (ii) hydrolyzing the resulting 4-heterocyclylthio-1-naphthol compound in the presence of a base to form a reaction product, and (iii) acidifying said reaction product.

2. The process of claim 1, wherein the 4-mercapto-1-naphthol compounds correspond to the formula (I)

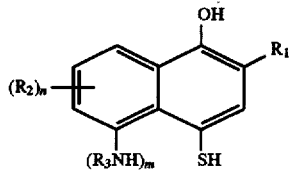

wherein $R_1$ represents —$CONR_4R_5$, —$NHCOR_4$, —$NHCOOR_6$, —$NHSO_2R_6$, —$NHCONR_4R_5$, or —$NHSO_2R_4R_5$, wherein $R_4$ and $R_5$ (which may be the same or different) each represents a hydrogen atom or an aliphatic, aromatic or heterocyclic group, or together $R_4$ and $R_5$ form a ring, and $R_6$ represents an aliphatic, aromatic or heterocyclic group, $R_2$ represents a group capable of substituting a hydrogen atom of the naphthol ring, n represents 0 or an integer of from 1 to 3 and, when n is 2 or 3, $R_2$'s can be the same or different, or together form a ring, $R_3$ represents a hydrogen atom or a monovalent organic group, and m represents 0 or 1.

3. The process of claim 1, wherein the 1-naphthol compound corresponds to the formula

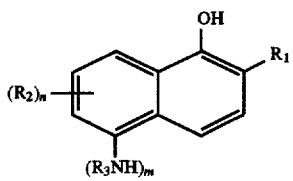

wherein $R_1$ represents —$CONR_4R_5$, —$NHCOR_4$, —$NHCOOR_6$, —$NHSO_2R_6$, —$NHCONR_4R_5$, or —$NHSO_2R_4R_5$, wherein $R_4$ and $R_5$ (which may be the same or different) each represents a hydrogen atom or an aliphatic, aromatic or heterocyclic group, or together $R_4$ and $R_5$ form a ring, and $R_6$ represents an aliphatic, aromatic or heterocyclic group, $R_2$ represents a group capable of substituting a hydrogen atom of the naphthol ring, n represents 0 or an integer of from 1 to 3 and, when n is 2 or 3, $R_2$'s can be the same or different, or together form a ring, $R_3$ represents a hydrogen atom or a monovalent organic group, and m represents 0 or 1.

4. The process of claim 1, wherein the heterocyclylsulfur chloride corresponds to the formula

wherein HET is a heterocyclic group.

5. The process of claim 1, wherein the 4-iodo-1-naphthol compound corresponds to the formula

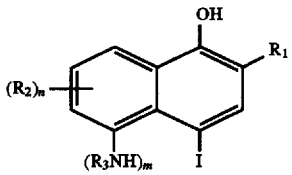

wherein $R_1$ represents —$CONR_4R_5$, —$NHCOR_4$, —$NHCOOR_6$, —$NHSO_2R_6$, —$NHCONR_4R_5$, or —$NHSO_2R_4R_5$, wherein $R_4$ and $R_5$ (which may be the same or different) each represents a hydrogen atom or an aliphatic, aromatic or heterocyclic group, or together $R_4$ and $R_5$ form a ring, and $R_6$ represents an aliphatic, aromatic or heterocyclic group, $R_2$ represents a group capable of substituting a hydrogen atom of the naphthol ring, n represents 0 or an integer of from 1 to 3 and, when n is 2 or 3, $R_2$'s can be the same or different, or together form a ring, $R_3$ represents a hydrogen atom or a monovalent organic group, and m represents 0 or 1.

6. The process of claim 1, wherein the alkali metal or ammonium salt of a mercaptoheterocyclic compound corresponds to the formula

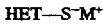

wherein HET represents a heterocyclic group and M represents an alkali metal or an ammonium group.

7. The process of claim 4 or 6, wherein said heterocyclic group is selected from the group consisting of tetrazolyl, triazinyl, triazolyl, oxazolyl, oxadiazolyl, diazolyl, thiazyl, thiadiazolyl, benzoxazolyl, benzotriazolyl, benzo-thiazolyl, pyrimidyl, pyrimidinyl and quinolinyl groups.

8. The process of claim 1, wherein the 4-heterocyclylthio-1-naphthol compound corresponds to the formula

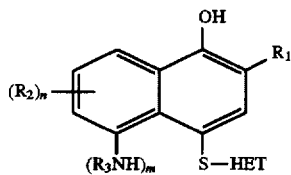

wherein

R$_1$ represents —CONR$_4$R$_5$, —NHCOR$_4$, —NHCOOR$_6$, —NHSO$_2$R$_6$, —NHCONR$_4$R$_5$, or —NHSO$_2$R$_4$R$_5$, wherein R$_4$ and R$_5$ (which may be the same or different) each represents a hydrogen atom or an aliphatic, aromatic or heterocyclic group, or together R$_4$ and R$_5$ form a ring, and R$_6$ represents an aliphatic, aromatic or heterocyclic group, R$_2$ represents a group capable of substituting a hydrogen atom of the naphthol ring, n represents 0 or an integer of from 1 to 3 and, when n is 2 or 3, R$_2$'s can be the same or different, or together form a ring, R$_3$ represents a hydrogen atom or a monovalent organic group, m represents 0 or 1, and HET is a heterocyclic group.

9. The process of claim 8, wherein said heterocyclic group is selected from the group consisting of tetrazolyl, triazinyl, triazolyl, oxazolyl, oxadiazolyl, diazolyl, thiazyl, thiadiazolyl, benzoxazolyl, benzotriazolyl, benzothiazolyl, pyrimidyl, pyrimidinyl and quinolinyl groups.

10. The process of claim 1, wherein the 4-mercapto-1-naphthol compounds are further reacted to obtain bleach accelerator releasing couplers having attached at the coupling position a releasable bleach accelerator group represented by the formula

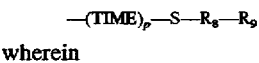

wherein

TIME is a timing group, p is 0 or 1,

R$_8$ is an alkylene group comprising 1 to 8 carbon atoms, and

R$_9$ is a water solubilizing group.

11. The process of claim 10, wherein the bleach accelerator releasing couplers correspond to the formula

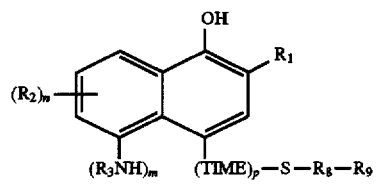

wherein

R$_1$ represents —CONR$_4$R$_5$, —NHCOR$_4$, —NHCOOR$_6$, —NHSO$_2$R$_6$, —NHCONR$_4$R$_5$, or —NHSO$_2$R$_4$R$_5$, wherein R$_4$ and R$_5$ (which may be the same or different) each represents a hydrogen atom or an aliphatic, aromatic or heterocyclic group, or together R$_4$ and R$_5$ form a ring, and R$_6$ represents an aliphatic, aromatic or heterocyclic group, R$_2$ represents a group capable of substituting a hydrogen atom of the naphthol ring, n represents 0 or an integer of from 1 to 3 and, when n is 2 or 3, R$_2$'s can be the same or different, or together form a ring, R$_3$ represents a hydrogen atom or a monovalent organic group, m represents 0 or 1, TIME is a timing group, p is 0 or 1, R$_8$ is an alkylene group comprising 1 to 8 carbon atoms, and R$_9$ is a water solubilizing group.

* * * * *